US012768754B2

(12) United States Patent
Ramakrishnan et al.

(10) Patent No.: US 12,768,754 B2
(45) Date of Patent: Oct. 20, 2026

(54) METHOD AND SYSTEM FOR MULTIPHASE FLUID SAMPLER USING TESLA VALVES

(71) Applicant: SAUDI ARABIAN OIL COMPANY, Dhahran (SA)

(72) Inventors: Vijay Ramakrishnan, Houston, TX (US); Garrett Malone, Houston, TX (US); Muhammad Arsalan, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 286 days.

(21) Appl. No.: 18/759,029

(22) Filed: Jun. 28, 2024

(65) Prior Publication Data

US 2026/0002847 A1 Jan. 1, 2026

(51) Int. Cl.
*G01N 1/20* (2006.01)
*G01N 1/22* (2006.01)
*G01N 33/28* (2006.01)

(52) U.S. Cl.
CPC ......... *G01N 1/2035* (2013.01); *G01N 1/2202* (2013.01); *G01N 1/2247* (2013.01); *G01N 33/2823* (2013.01); *G01N 2001/205* (2013.01)

(58) Field of Classification Search
CPC ... G01N 1/2035; G01N 1/2022; G01N 1/2247
USPC ....................................................... 73/863.41
See application file for complete search history.

(56) References Cited

U.S. PATENT DOCUMENTS 4,852,395 A * 8/1989 Kolpak .............. G01N 33/2823 73/861.04
2010/0031754 A1* 2/2010 Atkinson ............. G01N 1/2035 73/861.04

FOREIGN PATENT DOCUMENTS

CN 113325140 A 8/2021
EP 0 702 211 B1 12/1999
NO 346797 B1 1/2023

OTHER PUBLICATIONS

Nguyen, Quynh M. et al., "Early turbulence and pulsatile flows enhance diodicity of Tesla's macrofluidic valve"; Nature Communications; vol. 12, Article No. 2884; pp. 1-11; May 17, 2021 (11 pages).

(Continued)

*Primary Examiner* — Peter J Macchiarolo
*Assistant Examiner* — Rodney T Frank
(74) *Attorney, Agent, or Firm* — Osha Bergman Watanabe & Burton LLP

(57) ABSTRACT

A system includes a pipeline for flowing a fluid therein and a multiphase sampler fluidly coupled to the pipeline. The multiphase sampler includes an inlet to receive a fluid sample of the fluid from the pipeline, a Tesla valve(s) coupled between the pipeline and the inlet of the multiphase sampler to direct a flow of the fluid sample into a sensing section, and an outlet to return the fluid sample back into the pipeline. The sensing section includes at least one sensor to determine a water-cut of the fluid sample. A method includes flowing a fluid through a pipeline, streaming off a fluid sample from the fluid into an inlet of a multiphase sampler, determining a water-cut of the fluid sample in a sensing section of the multiphase sampler, and directing the fluid sample back into the pipeline.

20 Claims, 7 Drawing Sheets

(56) References Cited

OTHER PUBLICATIONS

Fluid Power Journal, "Tesla's Valvular Conduit"; Oct. 23, 2013; <https://fluidpowerjournal.com/teslas-conduit/>; Accessed Jun. 28, 2024 (14 pages).

* cited by examiner

METHOD AND SYSTEM FOR MULTIPHASE FLUID SAMPLER USING TESLA VALVES

BACKGROUND

In the oil and gas industry, fluids are typically produced from a reservoir in a formation by drilling a wellbore into the formation, establishing a flow path between the reservoir and the wellbore, and conveying the fluids from the reservoir to the surface through the wellbore. Typically, a production tubing is disposed in the wellbore to carry the fluids to the surface. At the surface, a pipeline may carry the produced fluids to various locations such as a separator or storage tank. The produced fluids may include hydrocarbons (e.g., oil and/or gas) and water. As the produced fluids may contain water, the ratio of hydrocarbons (e.g., oil and/or gas) to water may vary throughout the lifetime of the well. Conventionally, a multiphase flowmeter (MPFM) device is typically installed on the pipeline to measure the rate at which each phase (e.g., oil, gas, water) of the produced fluids is flowing. To that end, the MPFM device measures various fluid properties, such as a water-cut or water liquid ratio (WLR), of the produced fluids flowing through the MPFM device. The WLR is typically expressed as a percentage of the water volumetric flow rate over the liquid volumetric flow rate. The term “water liquid ratio” (WLR), strictly speaking, refers to the above ratio at pipeline conditions; the term ‘water-cut’, strictly speaking, refers to the above ratio at standard conditions. However, the two terms are often used interchangeably (including in the present disclosure). If the fluid properties (i.e., pressure-volume-temperature (PVT) properties) are known (and if the stages of separation are known), one can calculate water-cut from WLR (and vice versa).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a system. The system includes a pipeline for flowing a fluid therein; and a multiphase sampler fluidly coupled to the pipeline. The multiphase sampler includes an inlet to receive a fluid sample of the fluid from the pipeline; at least one Tesla valve coupled between the pipeline and the inlet of the multiphase sampler to direct a flow of the fluid sample into a sensing section, the sensing section having at least one sensor to determine a water-cut of the fluid sample; and an outlet to return the fluid sample back into the pipeline.

In another aspect, embodiments disclosed herein relate to a multiphase sampler. The multiphase sampler includes: an inlet to receive a fluid; at least one Tesla valve coupled to the inlet to direct a flow of the fluid into a sensing section coupled to the at least one Tesla valve; at least one sensor coupled to the sensing section to determine a water-cut of the fluid; and an outlet coupled to the sensing section to allow the fluid to exit the multiphase sampler.

In another aspect, embodiments disclosed herein relate to a method. The method includes flowing a fluid through a pipeline; streaming off a fluid sample from the fluid into an inlet of a multiphase sampler; flowing the fluid sample through at least one Tesla valve of the multiphase sampler; determining a water-cut of the fluid sample in a sensing section of the multiphase sampler; and directing the fluid sample back into the pipeline.

Other aspects and advantages of the claimed subject matter will be apparent from the following description and the appended claims.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, shapes of the elements as drawn are not necessarily intended to convey any information regarding the actual shape of the elements and have been solely selected for ease of recognition in the drawing.

DETAILED DESCRIPTION

Figure 1:
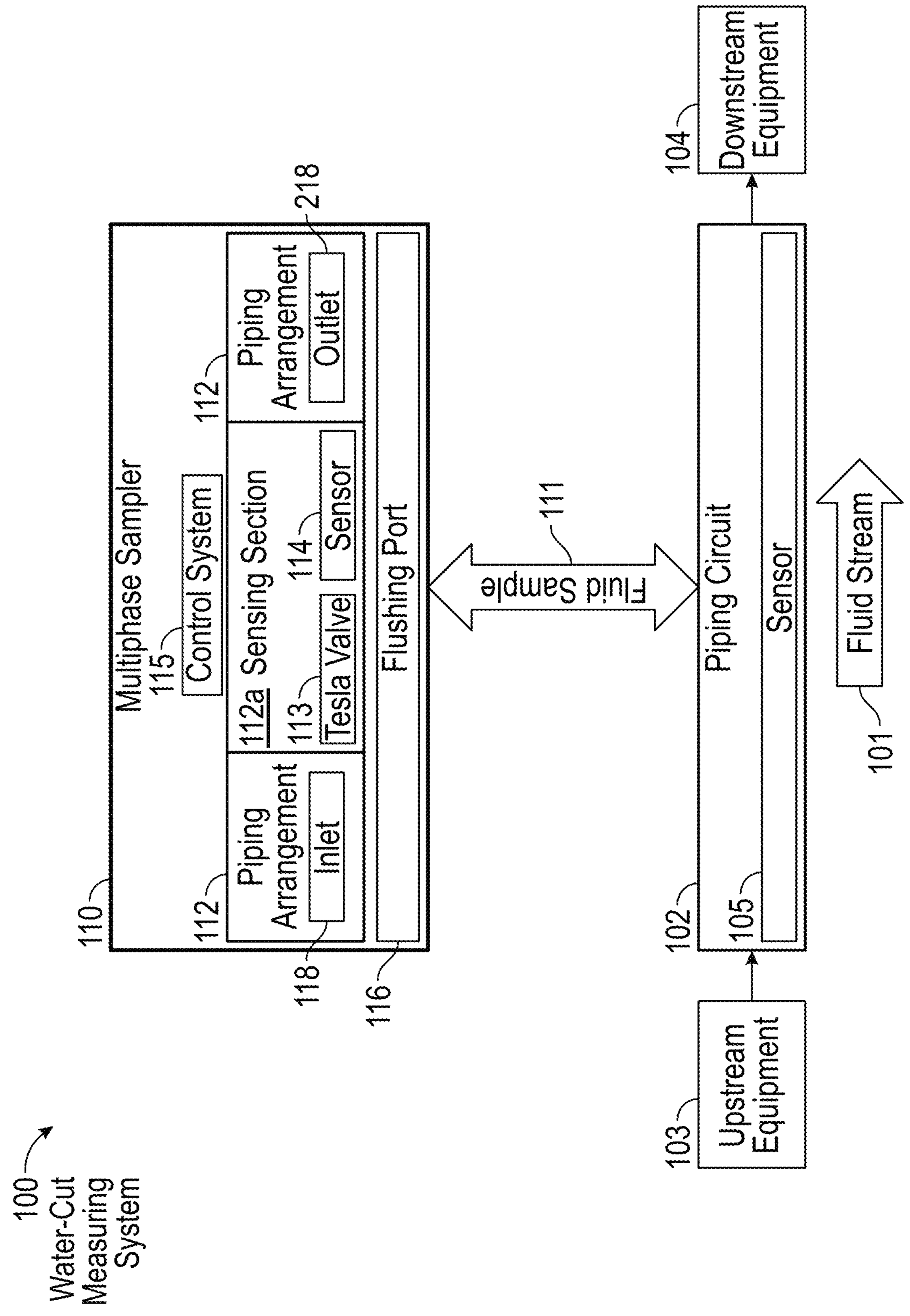
FIG. 1 illustrates a schematic diagram of a water-cut measuring system according to one or more embodiments of the present disclosure.

Embodiments of the present disclosure will now be described in detail with reference to the accompanying Figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

As used herein, the term “coupled” or “coupled to” or “connected” or “connected to” “attached” or “attached to” may indicate establishing either a direct or indirect connection and is not limited to either unless expressly referenced as such. Further, embodiments disclosed herein are described with terms designating a well site in reference to a land rig, but any terms designating rig type should not be deemed to limit the scope of the disclosure. For example, embodiments of the disclosure may be used on an offshore rig and various rig sites, such as land/drilling rig and drilling vessel. It is to be further understood that the various embodiments described herein may be used in various stages of a well, such as rig site preparation, drilling, completion, abandonment etc., and in other environments, such as work-over rigs, fracking installation, well-testing installation, and oil and gas production installation, without departing from the scope of the present disclosure. The embodiments are described merely as examples of useful applications, which are not limited to any specific details of the embodiments herein.

Conventional methods may use various techniques to measure the WLR. For example, gamma-ray attenuation methods, Coriolis methods, and near-infrared (NIR) absorption methods may be used to calculate the WLR. Gamma-ray attenuation methods use a beam (at a given energy level) passing through a representative portion of the produced fluids. The beam intensity attenuates as a function of the produced fluids' density. From this function, the WLR may be calculated for the produced fluids. However, in gamma-ray attenuation methods, a contrast between water and oil in the produced fluids is reduced when the gas content of the produced fluids is high. This results in increasing water-cut measurement errors during gamma-ray attenuation methods. In addition, devices for carrying out the gamma-ray attenuation methods require knowledge of gas fraction (either from a second gamma-energy level or another device), which introduces an additional source of measurement errors.

In Coriolis methods, a flow-tube (containing the produced fluids) is actively driven to a natural frequency, and then, the frequency of the flow-tube is measured. Since the natural frequency of a vibrating flow-tube is a function of density (i.e., tube and fluid combined) and a density of the flow-tube itself is known, the density of the produced fluids may be calculated. From this calculated density, the WLR may be calculated if the gas fraction of the produced fluids is known. While Coriolis methods are reliable when the phases of the produced fluids are all liquid (e.g., oil and/or water) they can be inaccurate in multiphase flows (i.e., when there is significant gas content in the produced fluids). For example, gas bubbles do not vibrate in-sync with the flow-tube (unlike liquids), and thus, the underlying physical relationship between flow-tube's natural frequency and the density of the produced fluids is weakened.

In NIR absorption methods, near-infrared radiation is passed through a representative portion of the produced fluids. An optical transmission of the near-infrared radiation is measured at specific near-infrared wavelengths which have high contrast between oil and water (in terms of absorption). This transmission/absorption measurement is a strong function of the WLR. Unlike Coriolis methods, NIR methods are typically better at handling high gas content, but due to the very high absorption levels (particularly with water) in the near-infrared spectrum, NIR absorption methods must use very small sensor-gaps (typically 1-3 mm wide). It is often difficult to get representative liquid samples of the produced fluids to flow though such small sensor-gaps, for example when the oil and water components are not well-mixed in the pipeline, resulting in erroneous readings.

Overall, the water-cut of the produced fluids is an important measurement for remote well-monitoring, reservoir management, and production optimization of a well. However, conventional methods to measure the water-cut are vulnerable under two main flow/fluid conditions: 1) when the gas content in the fluid sample is too high, beyond the method's operating envelope and/or 2) when the sensor is not positioned to interrogate a fluid sample that is representative in terms of water-oil ratio or WLR. Given the limitations of conventional methods, an apparatus that can side-stream a fluid sample whose liquid portion has same/similar water/oil ratio (i.e., WLR) as the main stream, while keeping most of the gas in the main stream, will be very beneficial.

In one or more embodiments, the present disclosure may be directed to systems and methods to a multiphase sampler using Tesla valves to measure a water-cut within a fluid stream of hydrocarbons from a well site. More specifically, the multiphase sampler includes a piping arrangement fluidly coupled to a flow line to take a fluid sample of a fluid stream flowing through the flow line. Additionally, at least one Tesla valve is provided within the piping arrangement to increase the liquid content of the fluid sample (i.e., liquid dominant to have more oil and water than gas) while also preventing backflow, especially in dynamic/pulsating flows with high pressure fluctuations. Furthermore, various sensors are provided on or within the piping arrangement to measure fluid properties of the fluid sample to determine the water-cut of the fluid sample. Further, the multiphase sampler may continuously measure the fluid properties of the fluid sample, determine the water-cut of the fluid sample, compare the results with a predetermined threshold of the water-cut, identify if a fluctuation pattern exists in the determined water-cut, and send alarms in case of fluctuation patterns. For example, the multiphase sampler may include a light that will flash when the fluctuation pattern exists, and the multiphase sampler may send a wireless signal to a control system and/or an operator to correct the fluctuation pattern. By using the multiphase sampler with Tesla valves, some embodiments may eliminate the need for using any moving parts and improve field implementation on a piping circuit.

Turning to FIG. 1, FIG. 1 shows a schematic diagram of a water-cut measuring system 100 in accordance with one or more embodiments. The water-cut measuring system 100 may be used to measure various fluid properties of a fluid stream 101 flowing through a piping circuit 102. The fluid stream 101 flows in the direction of the block arrow through the piping circuit 102. The fluid stream 101 may be a fluid produced from a well. For example, the fluid produced from the well may be a non-homogeneous mixture of phases of oil, gas, and water.

In one or more embodiments, the piping circuit 102 may be a flow line fluidly coupling upstream equipment 103 to downstream equipment 104. The fluid stream 101 exits the upstream equipment 103 and flows through the piping circuit 102 to the downstream equipment 104. For example, the upstream equipment 103 may be a wellhead, the downstream equipment 104 may be a separator or storage tank, and the piping circuit 102 may be a pipeline from the wellhead to the separator or storage tank. In some embodiments, the piping circuit 102, the upstream equipment 103, and the downstream equipment 104 may be any type of equipment that allows the fluid stream 101 to flow through from one to the other. For example, the equipment may be at a well site or plant such that the upstream equipment 103 and the downstream equipment 104 may be one or more of various hardware components, such as Christmas trees, blowout preventers, heat exchangers, pumps, valves, compressors, separators, dehydration units, stripping column, filters, processing equipment, production traps, mud pits, knockout vessels, desalters, loading racks, and storage tanks among various other types of hardware components for fluid flow.

As illustrated in FIG. 1, the water-cut measuring system 100 includes a multiphase sampler 110 to determine a water-cut of the fluid stream 101 flowing through the piping circuit 102. For example, the multiphase sampler 110 is fluidly coupled to the piping circuit 102 such that a fluid sample 111 of the fluid stream 101 is streamed off the piping circuit 102 to enter and flow through the multiphase sampler 110 and then back into the piping circuit 102. While the fluid sample 111 is flowing through the multiphase sampler 110, the multiphase sampler 110 measures various fluid properties to determine the water-cut of the fluid stream 101. In some embodiments, the fluid sample 111 may be a liquid-dominant sample (i.e., more liquid (oil and water) than gas) of the fluid stream 101. It is further envisioned that a gas-liquid fraction (or gas hold-up) of the fluid sample 111 does not need to be representative of the gas-liquid fraction of the fluid stream 101 (i.e., a main flow through the piping circuit 102) to accurately measure the water-cut of the fluid stream 101 from the fluid sample 111, because WLR, by definition, does not depend on gas content.

In one or more embodiments, the multiphase sampler 110 includes a piping arrangement 112 with at least one Tesla valve 113, and at least one sensor 114. For example, the piping arrangement 112 is a pipe or conduit to flow fluids therein. Additionally, the piping arrangement 112 may have various bends in any direction relative to a surface of the well, such as horizontal, vertical, or diagonal directions. To fluidly couple the multiphase sampler 110 to the piping circuit 102, the piping arrangement 112 includes an inlet 118 and an outlet 218 coupled to the piping circuit 102. The area in the piping arrangement 112 between the inlet 118 and the outlet 218 is referred to has a sensing section 112*a* of the multiphase sampler 110 which measures the various fluid properties of the fluid sample 111. It is further envisioned that the piping arrangement 112 has no major interruptions to the piping circuit 102 as most of the fluid stream 101 continues down the piping circuit 102 without entering the multiphase sampler 110. This provides a relatively low volume of the fluid sample 111 being side streamed from the fluid stream 101 into the multiphase sampler 110.

The inlet 118 of the piping arrangement 112 may be coupled to the piping circuit 102 at a location where the piping circuit 102 has a bend or elbow. Coupling the inlet 118 at the bend or elbow in the piping circuit 102 passively allows a well-mixed, representative (full-bore), liquid-dominant fluid sample 111 of the fluid stream 101 to enter the multiphase sampler 110. For example, the bend or elbow in the piping circuit 102 may be a bend in the pipe or conduit of the piping circuit 102 in a range of 45 to 180 degrees (i.e., a U-bend). In another embodiment, the inlet 118 of the piping arrangement 112 may include a sharp bend. In such a situation, the piping circuit 102 may be just a straight pipe where the sampler would be installed. The straight pipe may be modified to accommodate the bend and also accommodate the return connection to the piping circuit 102 from the sampler.

Additionally, the at least one Tesla valve 113 may be provided in or proximate to the inlet 118 of the piping arrangement 112 to ensure that a majority of the gas in the fluid stream 101 stays in the piping circuit 102 without entering the sensing section 112*a* of the multiphase sampler 110. Due to the bend and the at least one Tesla valve 113, the gas of the fluid stream 101 will take a flow path of least resistance to stay in the piping circuit 102, while the liquids of the fluid sample 111 enters the sensing section 112*a* of the multiphase sampler 110 due to the liquids' relatively higher inertia. The Tesla valves will determine how the flow is apportioned between the multiphase sampler 110 and the sample fluid stream. It is further envisioned that the inlet 118 of the piping arrangement 112 may be conical or funnel shaped to capture and direct the fluid sample 111 into the sensing section 112*a* of the multiphase sampler 110.

The outlet 218 of the piping arrangement 112 provides a pathway to return the fluid sample 111 back into the piping circuit 102 and the fluid stream 101. The outlet 218 of the piping arrangement 112 may be conical or funnel shaped to prevent backflow of fluid into the sensing section 112*a* of the multiphase sampler 110, especially in dynamic/pulsating flows with high pressure fluctuations. Additionally, the at least one Tesla valve 113 may be provided in or proximate to the outlet 218 of the piping arrangement 112 such that if any backflow occurs, the backflow will be a well-mixed, representative, liquid-dominant fluid sample to minimize contamination of the fluid sample 111 within the sensing section 112*a* of the multiphase sampler 110. By minimizing contamination of the fluid sample 111, the determined water-cut will be more accurate.

In one or more embodiments, the Tesla valve 113 is provided within the piping arrangement 112. For example, the Tesla valve 113 may be provided in or proximate the inlet 118 or outlet 218 of the piping arrangement 112. In some embodiments, when two Tesla valves (113) are provided within the piping arrangement 112, a first Tesla valve may be provided in or proximate the inlet 118 and a second Tesla valve may be provided in or proximate the outlet 218. The Tesla valve 113 has a fixed geometry to allow a fluid flow of the fluid sample 111 in one direction without moving parts. Examples of Tesla valves may be found in U.S. Pat. No. 1,329,559 or U.S. Pat. No. 10,245,586, which are incorporated by reference in their entireties herein. For example, the Tesla valve 113 includes a conduit provided with flow-control segments such as enlargements, recesses, projections, baffles, or buckets to restrict flow in one-direction. The flow-control segments of the Tesla valve 113 offer virtually no resistance to the fluid flow of the fluid sample 111 in one direction, other than surface friction, while providing an almost impassable barrier to its flow in the opposite direction. It is further envisioned that the Tesla valve 113 may be oriented in a forward or reverse direction. In the forward direction, the fluid sample 111 flows in a central corridor between the flow-control segments with only small lateral deflections. In the reverse direction, the fluid of the fluid sample 111 ricochets off the flow-control segments and deflects increasingly sharply before being rerouted around the flow-control segments and mixing within the central corridor between the flow-control segments. Tesla valves help mix fluids, whereas conventional check-valves do not help much. Conventional check-valves also have moving parts that can wear out or fail to actuate more easily over time; the Tesla valve does not wear easily and does not have moving parts. Additionally, for dynamic/pulsating flow (e.g., flow with fast-paced pressure fluctuations), conventional check-valves, like flapper valves, tend to rapidly open and close ("chatter") that could lead to an undesirable condition of amplified flow fluctuations in the sampler section.

Still referring to FIG. 1, the at least one sensor 114 is provided in the sensing section 112*a* of the multiphase sampler 110. The at least one sensor 114 may be, for example, a pressure sensor, a temperature sensor, a near-infrared (NIR) sensor, a microwave sensor, a gas-liquid level gauge, or a combination thereof. Additionally, one or more sensors 105 may be provided on the piping circuit 102 proximate both the inlet and outlet of the piping arrangement 112. The sensors 105 may be, for example, pressure and/or temperature sensors. By using the sensors 105, 114 in the piping circuit 102 and the sensing section 112*a* of the multiphase sampler 110, various fluid properties (such as density of oil ($\rho_{oil}$), density of water ($\rho_{water}$), and density of gas ($\rho_{gas}$)) of the fluid sample 111 and the fluid stream 101 may be measured. The water-cut can be corrected for pressure and temperature differences, determined by on the sensors 105, 114, between the piping circuit 102 and the sensing section 112*a* of the multiphase sampler 110. It is further envisioned that differential pressures may be measured across the Tesla valve 113 to infer flowrate into (and out of) the sensing section 112*a* of the multiphase sampler 110. The differential pressures across the Tesla valve 113 may be used to detect backflow and/or flow pulsations in the sensing section 112*a* of the multiphase sampler 110 and improve water-cut calculations (for example, flow-rate-weighted water-cut average).

In some embodiments, the sensing section 112*a* of the piping arrangement 112 may include a flushing port 116. The flushing port 116 may be a hole in the piping arrangement 112 that provides access to the Tesla valve 113 and/or the sensing section 112*a* of the multiphase sampler 110. For example, a line may be attached to the flushing port 116 to bleed pressure or unclog the Tesla valve 113 and/or the sensing section 112*a* of the multiphase sampler 110. The flushing port 116 may be used during periodic or on-demand system-maintenance activities of the multiphase sampler 110.

In one or more embodiments, the multiphase sampler 110 includes a control system 115 to receive the data from the sensors 105, 114 to determine the water-cut of the fluid sample 111. The control system 115 may be a programmable logic controller that is a ruggedized computer system with functionality to withstand vibrations, extreme temperatures, wet conditions, and/or dusty conditions, such as those around a refinery or drilling rig. Furthermore, the control system 115 may be a computer system similar to the computer system (602) described in FIG. 6 and the accompanying description. Accurate water measurement is directly linked with correct flow allocation to optimize production and provide efficient reservoir management. Determining the water-cut measurement on a wellhead may allow for the production choke to be adjusted accordingly to help reduce the water production by changing the back pressure. This measurement may also help the production engineer to determine how much oil and/or water they are likely to produce to match the production target and ensure the production rates are within the processing capacity of the gas oil separation plant. Determining a water-cut measurement in a downhole multilateral environment in intelligent wells may help determine the contribution of each lateral or specific zone within a lateral that can be controlled with inflow control valves, when available. Determining water-cut measurement within a facility may help to optimize the gas oil and water separation efficiency.

In some embodiments, to determine the water-cut of the fluid sample 111, the control system 115 may use various fluid parameters that are both known and measured of the fluid sample 111. For example, the fluid type of the fluid sample 111 which may include composition, molecular weights, density values, expansion factors regarding the compressibility or incompressibility of a fluid flow, etc. may be input into the control system 115. Additionally, the fluid flow rate of the fluid sample 111 may be measured through the piping arrangement 112 with the sensors 114. Furthermore, the sensing section 112*a* of the multiphase sampler 110 may use various methods (for example, level gauge, pressure differential, near-infrared (NIR), or microwaves) to measure the water-cut of the fluid sample.

Figure 3A:
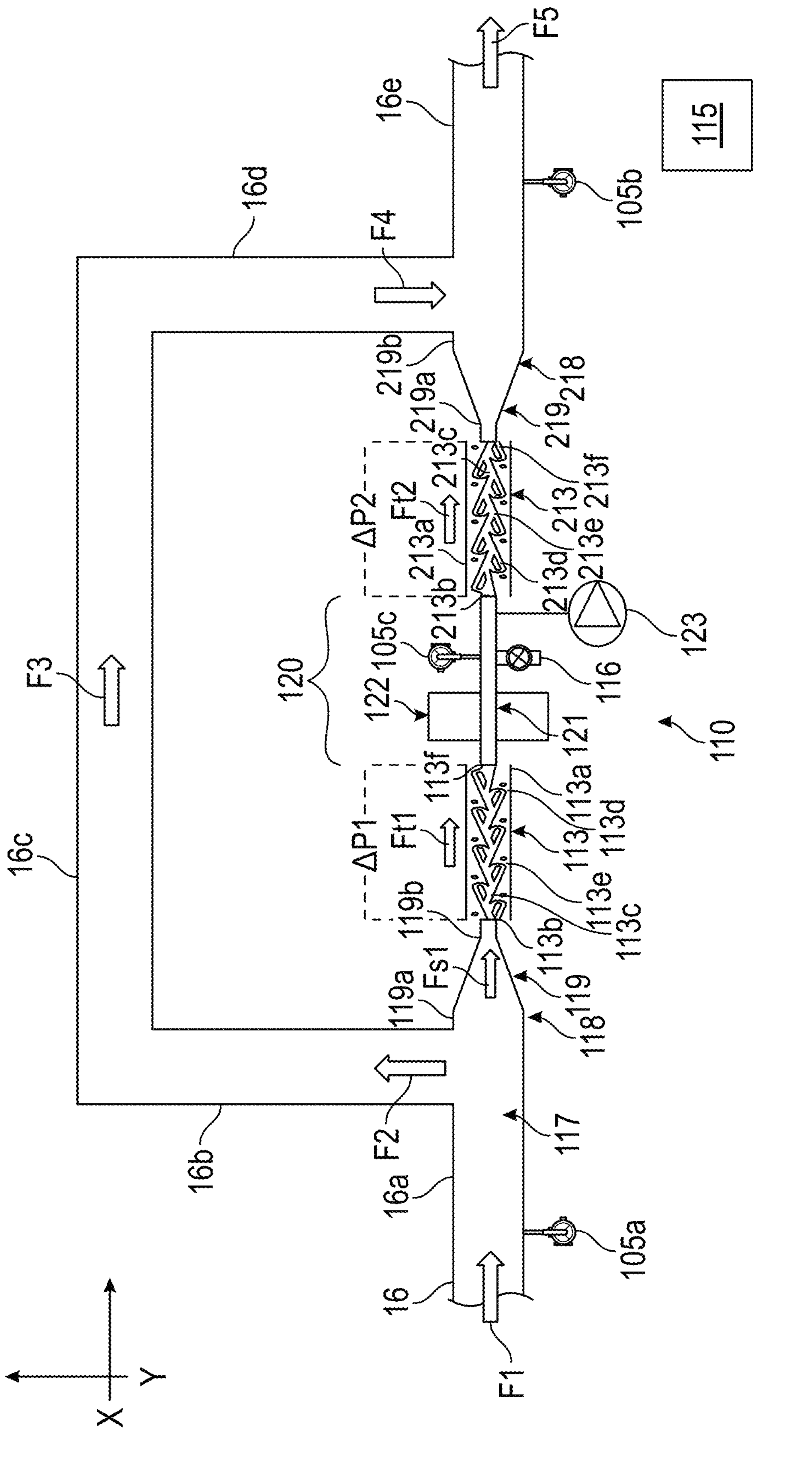
FIGS. 3A-3D illustrate close-up diagrams of the dotted box 3 from FIG. 2 according to one or more embodiments of the present disclosure.

In the embodiment shown in FIG. 3A, water-cut may be determined using an off-the-shelf sensor (such as NIR absorption or microwave resonance/transmission, etc.) installed in the sensing section 112*a* or a measurement section. For example, if a NIR-based water-cut sensor is used, the sensor is programmed before it is installed in the system with baseline absorption values of pure-oil and pure-water (at all NIR wavelengths of interest). In embodiments such as those shown in FIGS. 3B and 3C, water-cut may be determined using a differential pressure ΔP (across the fluid column of height 'h') and Equation 2. In this embodiment, the fluid parameters include pure-phase densities of oil, water, and gas. In one or more embodiments, collocated pressure and temperature sensors may be used to correct the pure-phase properties to local fluid conditions.

In some embodiments (such as FIG. 3A), for example, the determined water-cut corresponds to a continuously measured water-cut, from the sensors 105, 114, and can be enhanced using Equation 1 (below), which does a weighted-averaging of WLR using a measurement related to flow rate such as ΔP across the Tesla valve:

$$WLR_{avg} = \frac{\sum_k \left(WLR_k \cdot \sqrt{\Delta P1_k}\right)}{\sum_k \sqrt{\Delta P1_k}} \qquad \text{Equation 1}$$

where $WLR_{avg}$ corresponds to an average water-cut of the fluid sample 111, $\Delta P1_k$ corresponds to continuously measured differential pressure across the Tesla valve 113, $WLR_k$ corresponds to a continuously measured water-cut of the fluid sample 111, and k indicates an instant in time. In some embodiments (such as FIGS. 3B and 3C), for example, water-cut is determined from the following equation:

$$\frac{1}{g}\cdot\frac{\Delta P}{h} = \rho_{mix} = \rho_{gas}\cdot(1-\alpha_{liq}) + (\rho_{water}\cdot WLR + \rho_{oil}\cdot(1-WLR))\cdot\alpha_{liq} \qquad \text{Equation 2}$$

where g corresponds to acceleration due to gravity, ΔP corresponds to differential pressure over a column of the fluid sample 111 in the sensing section 112*a*, *h* corresponds to a height of the column of the fluid sample 111, $\rho_{mix}$ corresponds to a density of the fluid sample 111, $\rho_{gas}$ corresponds to a density of gas in the fluid sample 111, $\alpha_{liq}$ corresponds to a liquid fraction of the fluid sample 111. $\rho_{water}$ corresponds to a density of water in the fluid sample 111, WLR corresponds to a water-cut of the fluid sample 111, and $\rho_{oil}$ corresponds to a density of oil in the fluid sample 111. Liquid fraction $\alpha_{liq}$ is the volumetric ratio of liquid to total fluid, i.e., (volume of liquid)/(volume of liquid+volume of gas). Liquid-fraction ($\alpha_{liq}$) is measured from a gas-liquid level gauge 129, e.g., if the gas-liquid interface is at a depth 'y' from the top, then liquid-fraction ($\alpha_{liq}$)=h/(h+y).

Figure 2:
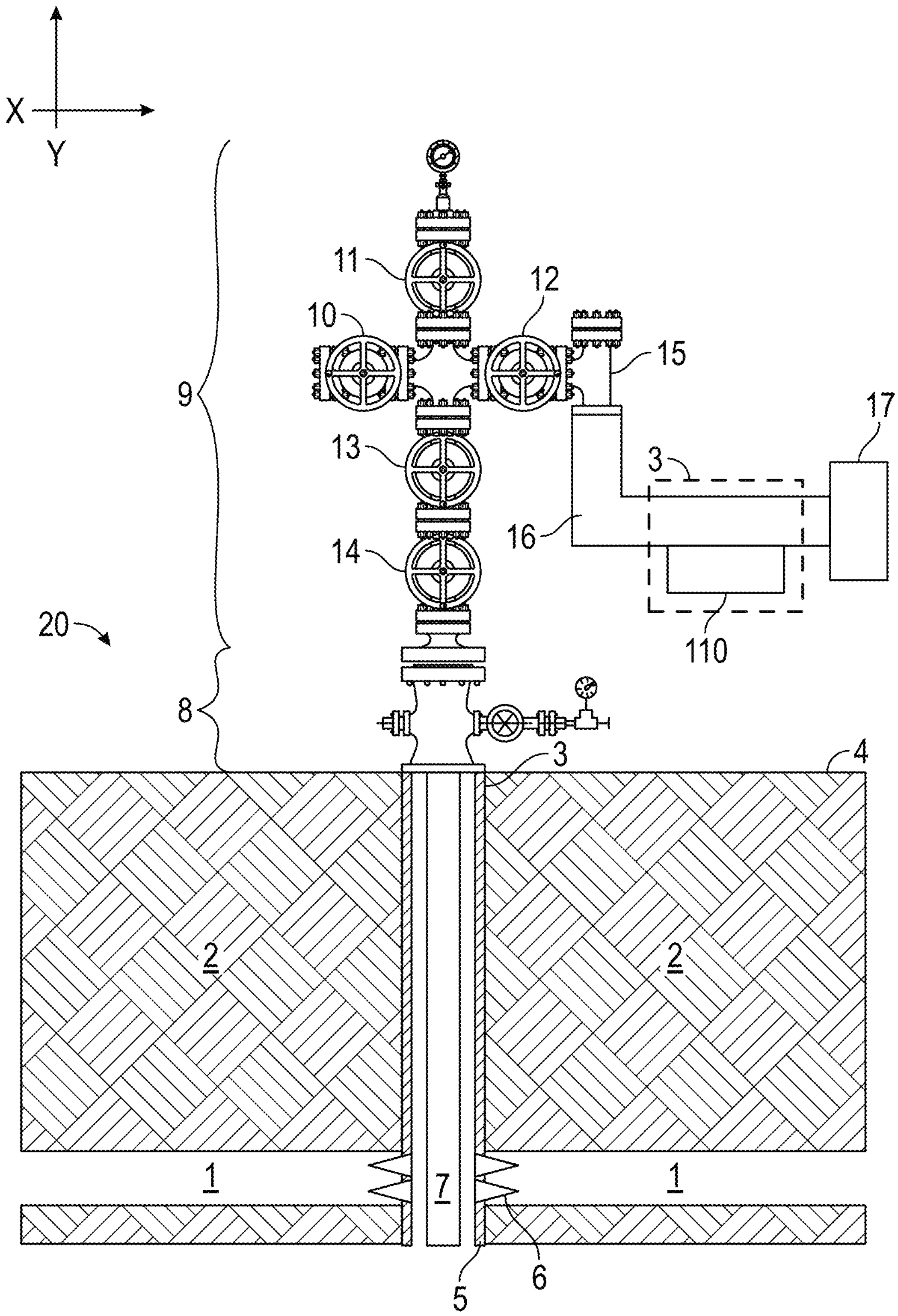
FIG. 2 illustrates a schematic diagram of a completion well using a water-cut measuring system according to one or more embodiments of the present disclosure.

Now referring to FIG. 2, a schematic diagram of a completion well 20 is illustrated in accordance with one or more embodiments. Fluids are produced from a reservoir 1 in a formation 2 by drilling a wellbore 3 into the formation 2, establishing a flow path between the reservoir 1 and the wellbore 3, and conveying the fluids from the reservoir 1 to a surface 4 through the wellbore 3. The produced fluids from the reservoir 1 may include a mixture of gas, oil, and water. A casing 5 may be installed in wellbore 3. In some embodiments, the casing 5 may be perforated such that perforations 6 in the casing allow a flow of the fluids from the reservoir 1 to enter the wellbore 3. Typically, a production tubing 7 is disposed in the wellbore 3 to carry the fluids to the surface 4. The production tubing 7 hangs from a wellhead 8 at the surface 4. The production tubing 7 extends to or past the reservoir 1, thereby forming a flow conduit from the reservoir 1 to surface 4.

A tree (also known as a Christmas tree) 9 is disposed on top of the wellhead 8 to control a flow of fluids into or out of the wellbore 3, depending on whether it is an injection well or a production well. The Christmas tree 9 includes a configuration of valves to control the fluids being injected into or pumped out of the wellbore 3. For example, the Christmas tree 9 may have an injection wing valve 10, a swab valve 11, a production wing valve 12, an upper master valve 13, and a lower master valve 14. When an operator is ready to conduct well operations the valves 10-14 are either opened or closed to control the fluids being injected into or pumped out of the wellbore 3. During injection, the production wing valve 12 and the swab valve 11 are closed while the injection wing valve 10, the upper master valve 13, and the lower master valve 14 are open to allow for fluids to be injected through the Christmas tree 9 and into the wellbore 3. During production, the injection wing valve 10 and the swab valve 11 are closed while the production wing valve 12, the upper master valve 13, and the lower master valve 14 are open to control or isolate fluid flow through a choke valve 15. From the choke valve 15, the produced fluids are transported, via a production flow line 16, to a separator 17 or to a production storage, transport, or facility. The production flow line 16 may be a pipeline extending in vertical (Y) and horizontal (X) directions with respect to the surface 4.

As shown in FIG. 2, a multiphase sampler 110 is fluidly coupled to the production flow line 16. The multiphase sampler 110 is used to determine a water-cut of the produced fluids at the surface 4. As shown in FIGS. 3A-3D, close-up views of the dotted box 3 in FIG. 2 illustrate cross-sectional views of various multiphase samplers 110 fluidly coupled to the production flow line 16.

In FIG. 3A, the produced fluids flow through (see block arrow F1) a first horizontal section **16*a* of the production flow line 16 towards the multiphase sampler 110. Before the multiphase sampler 110, the production flow line 16 may include a sharp bend or elbow 117 such that the bulk of the produced fluids continues flowing (see block arrow F2) up through a first vertical section 16*b* of the production flow line 16. From the first vertical section 16*b* of the production flow line 16, the bulk of the produced fluids flow past (see block arrow F3) the multiphase sampler 110 via a second horizontal section 16*c* of the production flow line 16. Next, the bulk of the produced fluids flow down (see block arrow F4) a second vertical section 16*d* of the production flow line 16 extending downward from the second horizontal section 16*c* of the production flow line 16. From the second vertical section 16*d* of the production flow line 16, the bulk of the produced fluids will flow away (see block arrow F5) from the multiphase sampler 110 via a third horizontal section 16*e* of the production flow line 16. It is noted that while portions (16*a*-16*e*) of the production flow line 16 are described as horizontal or vertical, those portions (16*a*-16*e*) of the production flow line 16 may be vertical or horizontal or at other angles with respect to the surface 4** without departing from the scope of the present disclosure.

In one or more embodiments, a first sensor **105*a* may be provided on the first horizontal section 16*a* of the production flow line 16 before the multiphase sampler 110 and a second sensor 105*b* may be provided on the third horizontal section 16*e* of the production flow line 16 after the multiphase sampler 110. The first sensor 105*a* and the second sensor 105*b* may be pressure and/or temperature sensors. The first sensor 105*a* and the second sensor 105*b* may be used to measure the pressure and temperature of the produced fluids before and after the multiphase sampler 110. Additionally, the first sensor 105*a* and the second sensor 105*b* may be used to measure various fluid properties (such as density of oil ($\rho_{oil}$), density of water ($\rho_{water}$), and density of gas ($\rho_{gas}$)) of the produced fluids. The control system 115 may receive pressure and temperature measurements from the first sensor 105*a* and the second sensor 105*b* and determine various fluid properties of the produced fluids based on the measured pressure and temperature. Further, both the first sensor 105*a* and the second sensor 105*b* may be wired to or wirelessly communicate with a control system 115. For example, the first sensor 105*a* and the second sensor 105*b* may send data to the control system 115 and receive commands from the control system 115**.

Figure 3B:
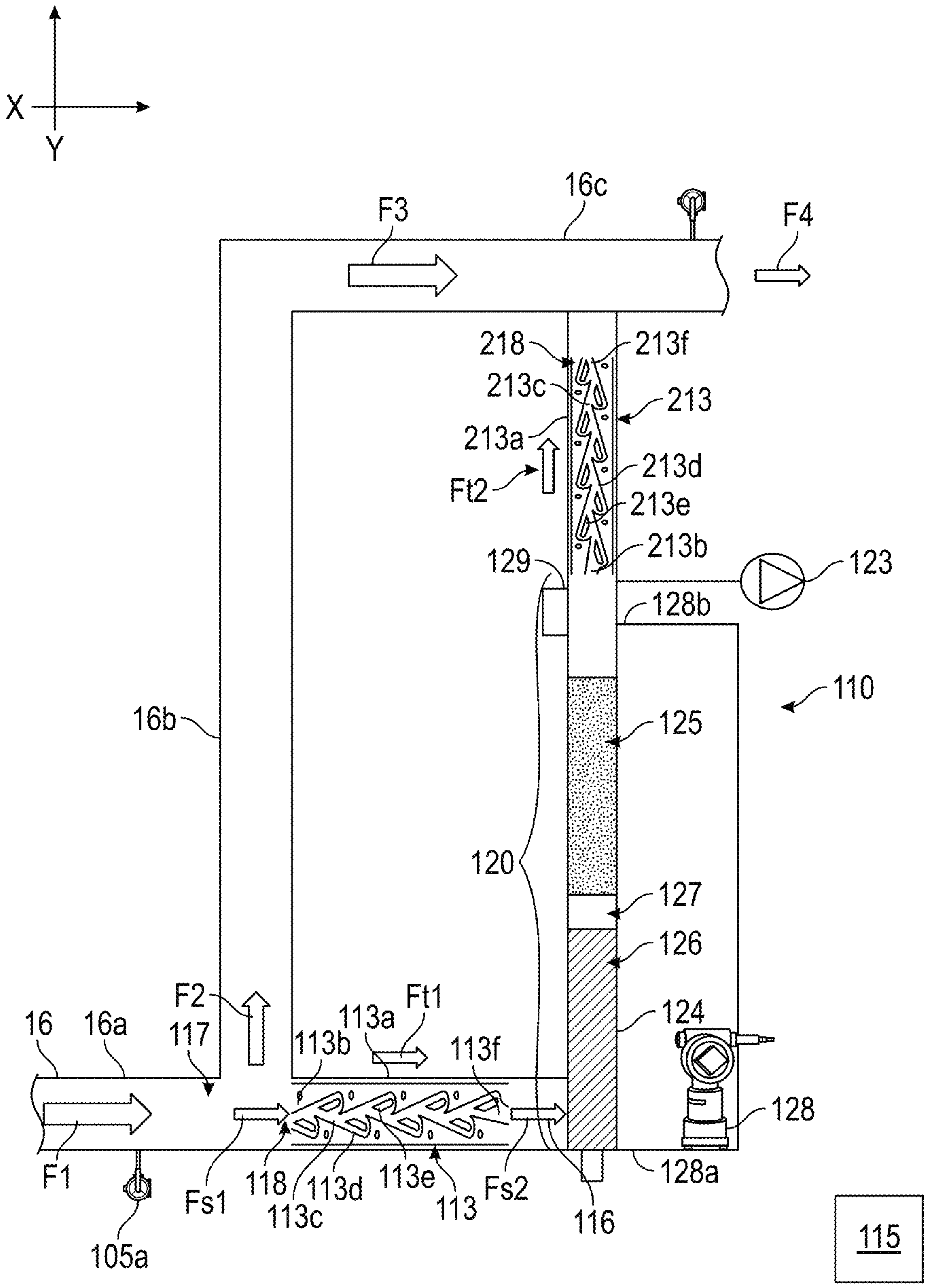

From the sharp bend or elbow 117, a fluid sample of the produced fluids is streamed off (see block arrow Fs1) into the multiphase sampler 110. For example, an inlet 118 of the multiphase sampler 110 is fluidly coupled to the sharp bend or elbow 117 to receive the fluid sample. The inlet 118 may be shaped to be a conical funnel 119 such that a diameter of the inlet 118 gets progressively smaller from the sharp bend or elbow 117 to a first Tesla valve 113 of the multiphase sampler 110. For example, the largest diameter of the inlet 118 is at a first end **119*a* of the conical funnel 119 adjacent to the sharp bend or elbow 117. From the first end 119*a*, the conical funnel 119 gets progressively smaller to a second end 119*b* to form the smallest diameter of the inlet 118 (i.e., the diameter at the first end 119*a* is a larger than the diameter at the second end 119*b*). The conical funnel 119 inlet 118 captures and directs an entire volume of the fluid sample into the first Tesla valve 113. The combination of the sharp bend or elbow 117 and the conical funnel 119 ensures that the fluid sample entering the first Tesla valve 113 is a well-mixed, representative (e.g., full-bore), liquid-dominant sample of the produced fluids. Another advantage of the conical funnel 119 is that it reduces the line size and therefore the size of the Tesla valve and the sampling section. The original "2-D" Tesla valve is typically more suitable for smaller line sizes. In another embodiment, the inlet 118 may not be shaped as a conical funnel 119, but rather may have a straight inlet like that shown in FIG. 3B. In other words, embodiments shown in FIGS. 3A and 3C may have inlets that are straight as shown in FIG. 3B. In embodiments having a straight inlet 118**, it may be more practical to use a "3-D" Tesla valve (such as the one disclosed in U.S. Pat. No. 10,245,586 or similar), because it is more compact than the "2-D" Tesla valve.

In one or more embodiments, from the conical funnel 119, the fluid sample flows through (see block arrow Ft1) a body **113*a* of the first Tesla valve 113. For example, an inlet 113*b* of the first Tesla valve 113 receives the fluid sample from the second end 119*b* of the conical funnel 119. The inlet 113*b* of the first Tesla valve 113 directs the fluid sample through a conduit 113*c* within the body 113*a* of the first Tesla valve 113. The conduit 113*c* includes flow-control segments (113*d*, 113*e*) to direct the fluid sample in the one direction (see block arrow Ft1). The flow-control segments (113*d*, 113*e*) may be formed by projections 113*d* extending radially inward from the conduit 113*c* and partitions 113*e* provided within the projections 113*d***.

Still referring to FIG. 3A, the first Tesla valve 113 may be oriented in a reverse direction to create high resistance and turbulence in the fluid sample flowing through the first Tesla valve 113. For example, the fluid sample will flow into the projections 113*d*, ricochet off the partitions 113*e*, deflect increasingly sharply before being rerouted around the partitions 113*e*, and mix within the conduit 113*c* (i.e., central passageway). The fluid sample will repeat the described flow path as the fluid sample continues to flow through the first Tesla valve 113. By having the first Tesla valve 113 oriented for a reverse direction flow path, the fluid sample will be further mixed before exiting an outlet 113*f* of the first Tesla valve 113.

From the outlet 113*f* of the first Tesla valve 113, the fluid sample will exit the first Tesla valve 113 and flow into a sensing section 120 of the multiphase sampler 110. In the sensing section 120, the fluid sample flows through a pipe 121. For example, an end of the pipe 121 is fluidly coupled to the outlet 113*f* of the first Tesla valve 113. From the first Tesla valve 113, the pipe 121 may extend axially in a horizontal direction of the plane P to a second Tesla valve 213.

In sensing section 120, a water-cut sensor 122 is fluidly attached to the pipe 121 to measure the water-cut of the fluid sample. For example, the water-cut sensor 122 may be a near-infrared (NIR) or microwave sensor. With the near-infrared (NIR) or microwave sensor (122), the water-cut sensor 122 will pass radiation through the fluid sample in the pipe 121. The water-cut sensor 122 will then measure an optical transmission of the radiation at specific wavelengths which correlates to the water-cut of the fluid sample. Additionally, the water-cut sensor 122 may be wired to or wirelessly communicate with the control system 115. For example, the water-cut sensor 122 may send data to the control system 115 and receive commands from the control system 115.

In some embodiments, a third sensor 105*c* may be provided on the pipe 121. The third sensor 105*c* may be downstream of the water-cut sensor 122. The third sensor 105*c* may be a pressure and/or temperature sensor to measure the pressure and/or temperature of the fluid sample in the sensing section 120. Additionally, the third sensor 105*c* may be used to measure various fluid properties (such as density of oil ($\rho_{oil}$), density of water ($\rho_{water}$), and density of gas ($\rho_{gas}$)) of the fluid sample. The control system 115 may receive pressure and temperature measurement from the third sensor 105*c* and determine various fluid properties of the produced fluids based on the measured pressure and temperature. Further, the third sensor 105*c* may be wired or wirelessly communicate with the control system 115. For example, the third sensor 105*c* may send data to the control system 115 and receive commands from the control system 115.

In one or more embodiments, a flushing port 116 may be installed on the pipe 121. The flushing port 116 is used during periodic or on-demand system-maintenance activities to unclog (if needed) the Tesla valves (113, 213) and/or the sensing section 120. For example, the flushing port 116 may be a hole in the pipe 121 that provides access to the Tesla valves (113, 213) and/or the sensing section 120. The flushing port 116 may be opened to bleed pressure or unclog the Tesla valves (113, 213) and/or the sensing section 120.

As shown in FIG. 3A, from the sensing section 120, the fluid sample flows into the second Tesla valve 213. The second Tesla valve 213 is fluidly coupled to an end of the pipe 121 distal to the first Tesla valve 113. For example, an inlet 213*b* of the second Tesla valve 213 is fluidly attached to the pipe 121. As the fluid sample flows through (see block arrow Ft2) a body 213*a* of the second Tesla valve 213, the second Tesla valve 213 prevents a backflow of the fluid sample flowing back into the sensing section 120, especially in dynamic/pulsating flows with high pressure fluctuations. For example, the second Tesla valve 213 may be oriented in a forward direction to have the flow (see block arrow Ft2) in one direction. In the forward direction, the fluid sample flows in a conduit 213*c* (i.e., central passageway) of the second Tesla valve 213 between projections 213*d* and partitions 213*e* (i.e., flow-control segments) of the second Tesla valve 213 with only small lateral deflections. By having the second Tesla valve 213 oriented for a forward direction flow path, fluids flow from the production flow line 16 will be restricted or prevented from back flowing into the multiphase sampler 110 via an outlet 213*f* of the second Tesla valve 213.

In some embodiments, a first differential pressure ΔP1 may be taken across the first Tesla valve 113, from the inlet 113*b* to the outlet 113*f*. The first differential pressure ΔP1 may be used to determine a flow rate of the fluid sample flow into the sensing section 120 from the first Tesla valve 113. Additionally, a second differential pressure ΔP2 may be taken across the second Tesla valve 213, from the inlet 213*b* to the outlet 213*f*. The second differential pressure ΔP2 may be used to determine a flow rate of the fluid sample flow out of the sensing section 120 into the second Tesla valve 213. To measure the pressure, each differential pressure sensor may be connected to the pipe 121 via two impulse tubings (not shown). In this example, one tubing connects to a port on the pipe just before the Tesla valve. Another tubing connects to a port on the pipe just after the Tesla valve. By measuring the first differential pressure ΔP1 and the second differential pressure ΔP2, backflow and flow pulsations in the sensing section 120 may be detected and corrected to improve water-cut measurements. The water-cut measurements taken by the water-cut sensor 122 may be averaged over the determined flow rates to form a flow-rate-weighted water-cut average. The control system 115 uses Equation 1 to calculate the flow-rate-weighted water-cut average of the fluid sample.

From the second Tesla valve 213, the fluid sample will flow back into the production flow line 16 via an outlet 218 of the multiphase sampler 110. The outlet 218 of the multiphase sampler 110 is fluidly coupled to a portion of the production flow line 16 that bypasses the multiphase sampler 110. As shown in FIG. 3A, the outlet 218 of the multiphase sampler 110 is fluidly coupled to the third horizontal section 16*e* of the production flow line 16 to return the fluid sample to the production flow line 16. The outlet 218 may include a conical shaped reverse funnel 219 such that a diameter of the outlet 218 gets progressively larger from the second Tesla valve 213 to the third horizontal section 16*e* of the production flow line 16. For example, the smallest diameter of the outlet 218 is at a first end 219*a* of the conical funnel 219 adjacent to the second Tesla valve 213. From the first end 219*a*, the conical shaped reverse funnel 219 gets progressively larger to a second end 219*b* to form the largest diameter of the outlet 218 (i.e., the diameter at the first end 219*a* is a smaller than the diameter at the second end 219*b*). The conical shaped reverse funnel 219 outlet 218 captures and directs a volume of the fluid sample into the third horizontal section 16*e* of the production flow line 16. It is further envisioned that if there is any backflow into the multiphase sampler 110, the combination of the conical shaped reverse funnel 219 outlet 218 and the second Tesla valve 213 ensures that any backflow entering the sensing section 120 is well-mixed, representative (e.g., full-bore), liquid-dominant sample of the produced fluids. This will minimize contamination of the fluid samples in the sensing section 120 and reduce the backflow's impact on the water-cut measurement.

In some embodiments, a pump 123 may be fluidly coupled to the sensing section 120. The pump may provide more control on the volume of fluids (and their residence time) in the sensing section, e.g., the pump can help ensure that the column is sufficiently full (and representative of WLR in the piping circuit 102).

The pump 123 may be run continuously or intermittently to ensure that the fluid sample is returned to the production flow line 16. For example, the pump 123 may have one end fluidly coupled to the pipe 121 downstream of the water-cut sensor 122 and upstream of the second Tesla valve 213. In operation, the pump 123 may be turned on to pump the fluid sample through the second Tesla valve 213.

Referring now to FIG. 3B, another embodiment of a multiphase sampler 110 according to embodiments herein is illustrated, where like numerals represent like parts. The embodiment shown in FIG. 3B includes a multiphase sampler 110 with a sensing section 120 between two Tesla valves (113, 213) and the sensing section 120 includes a bend to form a vertical column 124. Additionally, a first Tesla valve 113 is oriented horizontally and a second Tesla valve 213 is oriented vertically. In FIG. 3B, the produced fluids flow through (see block arrow F1) a first horizontal section 16*a* of the production flow line 16 towards the multiphase sampler 110. Before the multiphase sampler 110, the production flow line 16 may include a sharp bend or elbow 117 such that the bulk of the produced fluids continues flowing (see block arrow F2) up through a first vertical section 16*b* of the production flow line 16. From the first vertical section 16*b* of the production flow line 16, the bulk of the produced fluids flow past (see block arrow F3) the multiphase sampler 110 via a second horizontal section 16*c* of the production flow line 16. From the second horizontal section 16*c* of the production flow line 16, the bulk of the produced fluids will flow away (see block arrow F4) from the multiphase sampler 110.

In one or more embodiments, a first sensor 105*a* may be provided on the first horizontal section 16*a* of the production flow line 16 before the multiphase sampler 110 and a second sensor 105*b* may be provided on the second horizontal section 16*c* of the production flow line 16 after the multiphase sampler 110. The first sensor 105*a* and the second sensor 105*b* may be pressure and/or temperature sensors. The first sensor 105*a* and the second sensor 105*b* may be used to measure the pressure and/or temperature of the produced fluids before and after the multiphase sampler 110. Additionally, the first sensor 105*a* and the second sensor 105*b* may be used to measure various fluid properties (such density of oil ($\rho_{oil}$), density of water ($\rho_{water}$), and density of gas ($\rho_{gas}$)) of the produced fluids. The control system 115 may receive pressure and temperature measurement from the first sensor 105*a* and the second sensor 105*b* and determine various fluid properties of the produced fluids based on the measured pressure and temperature, Further, both the first sensor 105*a* and the second sensor 105*b* may be wired to or wirelessly communicate with a control system 115. For example, the first sensor 105*a* and the second sensor 105*b* may send data to the control system 115 and receive commands from the control system 115.

From the sharp bend or elbow 117, a fluid sample of the produced fluids is streamed off (see block arrow Fs1) into the multiphase sampler 110. For example, an inlet 118 of the multiphase sampler 110 is fluidly coupled to the sharp bend or elbow 117 to receive the fluid sample. As shown in FIG. 3B, the inlet 118 of the multiphase sampler 110 is also an inlet 113*b* of a first Tesla valve 113. Through the inlet 113*b* of the first Tesla valve 113, the fluid sample flows through (see block arrow Ft1) a body 113*a* of the first Tesla valve 113. For example, the inlet 113*b* of the first Tesla valve 113 directs the fluid sample through a conduit 113*c* within the body 113*a* of the first Tesla valve 113. The conduit 113*c* includes flow-control segments (113*d*, 113*e*) to direct the fluid sample in the one direction (see block arrow Ft1). The flow-control segments (113*d*, 113*e*) may be formed by projections 113*d* extending radially from the conduit 113*c* and partitions 113*e* provided within the projections 113*d*.

In some embodiments, the first Tesla valve 113 may be oriented in a reverse direction to provide high resistance and turbulence in the fluid sample flowing through the first Tesla valve 113. For example, the fluid sample will flow into the projections 113*d*, ricochet off the partitions 113*e*, deflect increasingly sharply before being rerouted around the partitions 113*e*, and mix within the conduit 113*c* (i.e., central passageway). The fluid sample will repeat the described flow path as the fluid sample continues to flow through the first Tesla valve 113. By having the first Tesla valve 113 oriented for a reverse direction flow path, the fluid sample will be further mixed before exiting an outlet 113*f* of the first Tesla valve 113. The first Tesla valve 113 ensures that the fluid sample entering the first Tesla valve 113 is well-mixed, representative (e.g., full-bore), liquid-dominant sample of the produced fluids. Additionally, the first Tesla valve 113 allows the fluid sample to trickle in, continuously feed (see block arrow Fs2) into a sensing section 120 of the multiphase sampler 110. It is further envisioned that the first Tesla valve 113 blocks most of a gas volume of the produced fluids from entering the sensing section 120 of the multiphase sampler 110. For example, the high resistance and turbulence created by having the first Tesla valve 113 oriented in the reverse direction forms a gas resistive flow path as the gas volume of the produced fluids will flow in the least resistive path, i.e., the production flow line 16.

Still referring to FIG. 3B, the sensing section 120 of the multiphase sampler 110 may be a column 124 extending in a vertical direction of the plane P. In the vertical column 124, the fluid sample may separate over time due to gravity. For example, a gas volume 125 of the fluid sample will partially separate from a liquid volume 126 of the fluid sample. The liquid volume 126 of the fluid sample will settle towards a bottom of the vertical column 124 while the gas volume 125 of the fluid sample will settle on top of the liquid volume 126 of the fluid sample. Additionally, there may be a transition zone 127 in the vertical column 124 where the liquid volume 126 of the fluid sample interacts with the gas volume 125 of the fluid sample. By having the gas volume 125 of the fluid sample separated from the liquid volume 126 of the fluid sample, the vertical column 124 will always contain a time-averaged representative water-cut sample of the produced fluids.

In one or more embodiments, the vertical column 124 may include one or more sensors (128, 129). For example, a differential-pressure sensor 128 may have a first line 128*a* attached to the bottom end of the vertical column 124 and a second line 128*b* attached to a top end of the vertical column 124 to measure a differential pressure of the fluid sample in the vertical column 124. Additionally, a gas-liquid level gauge 129 may be attached near the top end of the vertical column 124 to measure a height of the liquid volume 126 and the gas volume 125 in the vertical column 124. Additionally, both the differential-pressure sensor 128 and the gas-liquid level gauge 129 may be wired to or wirelessly communicate with the control system 115. For example, the differential-pressure sensor 128 and the gas-liquid level gauge 129 may send data to the control system 115 and receive commands from the control system 115. With measurements from the differential-pressure sensor 128 and the gas-liquid level gauge 129, the control system 115 determines a water-cut of the fluid sample.

In some embodiments, a flushing port 116 may be installed on the bottom end of the vertical column 124. The flushing port 116 is used during periodic or on-demand system-maintenance activities to unclog (if needed) the Tesla valves (113, 213) and/or the sensing section 120. For example, the flushing port 116 may be a hole in the vertical column 124 that provides access to the Tesla valves (113, 213) and/or the sensing section 120. The flushing port 116 may be opened to bleed pressure or unclog the Tesla valves (113, 213) and/or the sensing section 120.

As shown in FIG. 3B, from the sensing section 120, the fluid sample flows upward through a second Tesla valve 213. Pressure in the first horizontal section 16*a* of the production flow line 16 is sufficient to drive the fluid upward thorough the Tesla valve 213. For example, in one or more embodiments, the pressure in a typical production flow line is 200 psig to 1500 psig or greater. The second Tesla valve 213 is fluidly coupled to the top end of the vertical column 124. For example, an inlet 213*b* of the second Tesla valve 213 is fluidly attached to the top end of the vertical column 124. As the fluid sample flows through (see block arrow Ft2) a body 213*a* of the second Tesla valve 213, the second Tesla valve 213 prevents a backflow of the fluid sample flowing back into the vertical column 124, especially in dynamic/pulsating flows with high pressure fluctuations. For example, the second Tesla valve 213 may be oriented in a forward flow direction from the sensing section 120 toward the production flow line 16 to have the flow (see block arrow Ft2) in one direction. In the forward direction, the fluid sample flows in a conduit 213*c* (i.e., central passageway) of the second Tesla valve 213 between projections 213*d* and partitions 213*e* (i.e., flow-control segments) of the second Tesla valve 213 with only small lateral deflections. Orienting the second Tesla valve 213 for a forward direction flow path restricts or prevents backflow from the production flow line 16 into the multiphase sampler 110 via outlet 213*f* of the second Tesla valve 213, especially in dynamic/pulsating flows with high pressure fluctuations.

From the second Tesla valve 213, the fluid sample will return to the production flow line 16 via outlet 218 of the multiphase sampler 110. For example, the outlet 218 of the multiphase sampler 110 is fluidly coupled to the second horizontal section 16*c* of the production flow line 16 to receive the fluid sample. The outlet 218 of the multiphase sampler 110 is also the outlet 213*f* of the second Tesla valve 213.

In some embodiments, a pump 123 may be fluidly coupled to the sensing section 120. The pump 123 may be run continuously or intermittently to ensure that the fluid sample in the sensing section 120 is returned to the production flow line 16. For example, the pump 123 may have one end fluidly coupled to the top end of the vertical column 124 and upstream of the second Tesla valve 213. In operation, the pump 123 may be turned on to pump the fluid sample through the second Tesla valve 213 and into the production flow line 16.

Figure 3C:
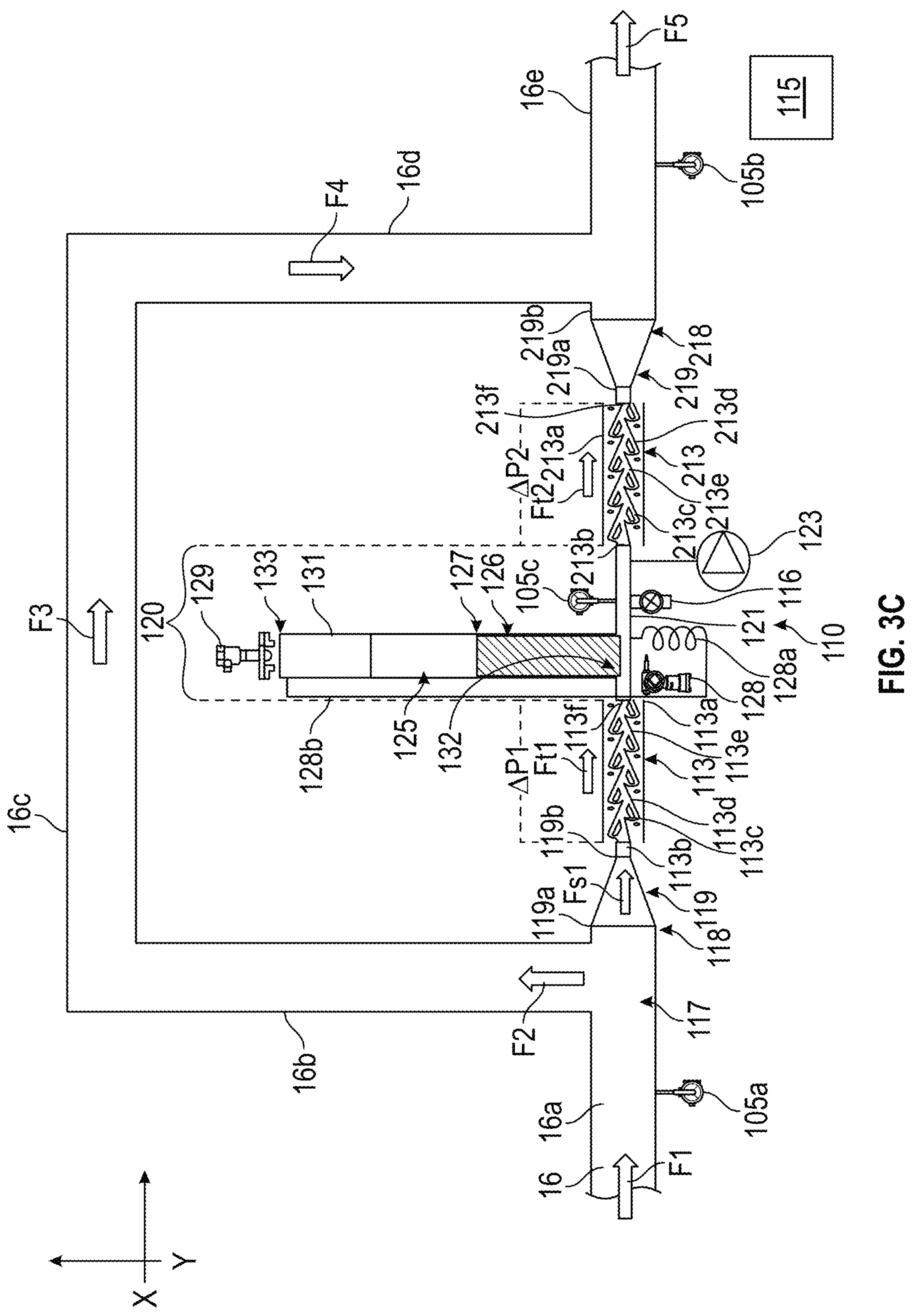

Referring now to FIG. 3C, another embodiment of a multiphase sampler 110 according to embodiments herein is illustrated, where like numerals represent like parts. The embodiment of FIG. 3C is similar to that of the embodiment of FIG. 3A. However, in place of the water-cut sensor (see 122 in FIG. 3A), the sensing section 120 includes a column or chamber 131 extending upward from the pipe 121. For example, the column or chamber 131 includes an opening 132 in fluid communication with the pipe 121. From the pipe 121, the column or chamber 131 extends upward to a capped end 133 distal the opening 132. Additionally, in FIG. 3C, instead of the first Tesla valve being oriented in a reverse direction (see 113 in FIG. 3A), the first Tesla valve 313 is oriented in a forward direction. By having the first Tesla valve 313 in the forward direction, backflow from the column or chamber 131 is restricted or prevented, especially in dynamic/pulsating flows with high pressure fluctuations.

In the embodiment of FIG. 3C, a fluid sample is streamed off from the production flow line 16 into the multiphase sampler 110, through the first Tesla valve 313 to the column or chamber 131. The fluid sample will fill the column or chamber 131 in the sensing section 120. Additionally, a pump 123 coupled to pipe 121 of the sensing section 120 may need to be stopped to allow for the fluid sample to fill the column or chamber 131. For example, the pump 123 may be continuously run to flow the fluid sample through the multiphase sampler 110, and then the pump 123 may be stopped (on demand) to allow a fluid sample to fill up the column or chamber 131 over a period of time. This will trap the fluid sample in the column or chamber 131. In the column or chamber 131, the gas volume 125 and the liquid volume 126 of the fluid sample will separate. To measure the water-cut of the trapped fluid sample, first, a liquid-level of the liquid volume 126 is measured using the gas-liquid level gauge 129 (e.g., sonic pulse or electromagnetic/radar ping). Next, a liquid-fraction ($\alpha_{liq}$) of the trapped fluid sample in the column or chamber 131 is calculated. For example, the control system 115 compares the liquid-level of the liquid volume 126 to the gas volume 125 to determine how much volume of the fluid sample in the column or chamber 131 is a liquid (i.e., the liquid-faction ($\alpha_{liq}$)). In some embodiments, the liquid-level measurement may be obtained by extrapolation over time (e.g., exponential asymptote), if needed, without waiting for full gas-liquid separation in the column or chamber 131. Finally, the control system 115 calculates a water-cut of the fluid sample with the pressure differential across the entire column or chamber 131 using Equation 2 above. Once the water-cut is determined, the pump 123 may be turned on to empty the column or chamber 131 and return the fluid sample back to the production flow line 16.

Figure 3D:
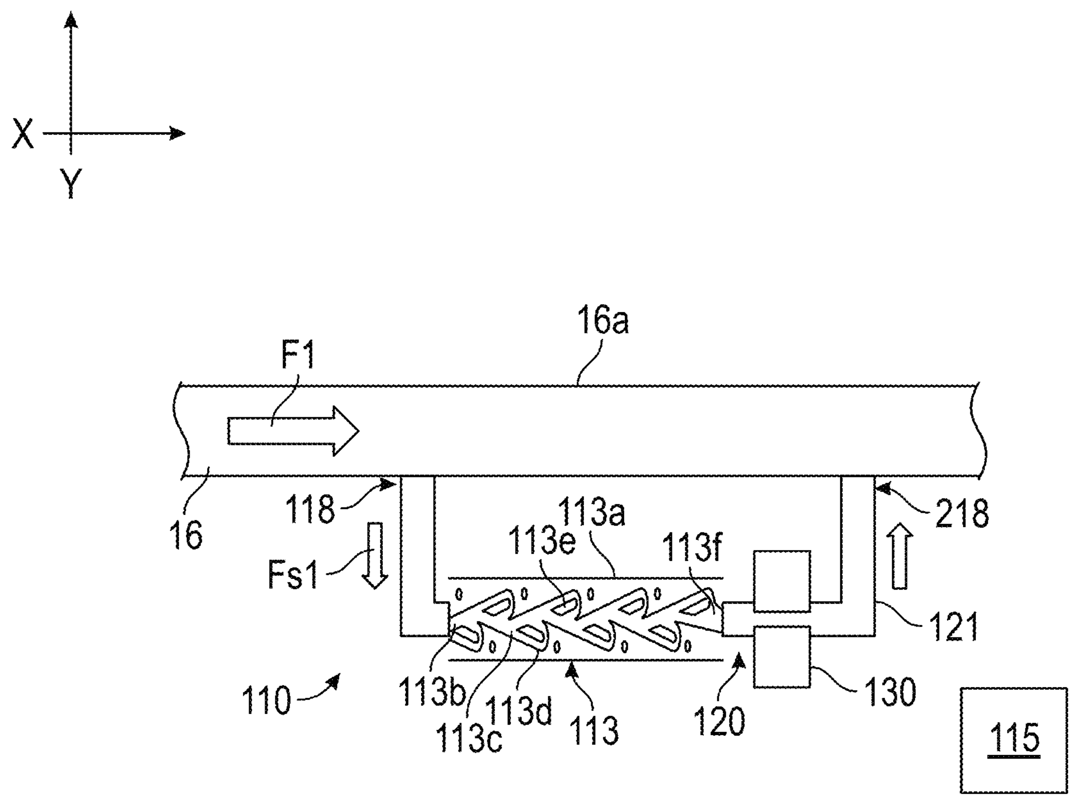

Referring now to FIG. 3D, another embodiment of a multiphase sampler 110 according to embodiments herein is illustrated, where like numerals represent like parts. The multiphase sampler 110 of FIG. 3D may be used in stratified horizontal flows to obtain a water-weighted liquid subsample which can be analyzed for salinity measurements. For example, the produced fluids flow through (see block arrow F1) a horizontal section 16*a* of the production flow line 16 towards the multiphase sampler 110. From the horizontal section 16*a* of the production flow line 16, a fluid sample of produced fluids will be side streamed off (see block arrow Fs1) into the multiphase sampler 110. For example, an inlet 118 of the multiphase sampler 110 is fluidly coupled to the horizontal section 16*a* of the production flow line 16 such that the fluid sample is automatically side streamed (see block arrow Fs1) into the multiphase sampler 110.

In one or more embodiments, the multiphase sampler 110 is affixed below the horizontal section 16*a* of the production flow line 16. This creates a natural gravity feed into the inlet 118 of the multiphase sampler 110. As the produced fluids are flowing through the horizontal section 16*a* of the production flow line 16, gravity will naturally separate the produced fluids to form a stratified horizontal flow (i.e., gas will flow on top of liquids). By having the stratified horizontal flow, the natural gravity fed flow will automatically pull a liquid-dominant fluid sample into the inlet 118 as the multiphase sampler 110 is affixed below the horizontal section 16*a*.

From the inlet 118 of the multiphase sampler 110, the fluid sample will flow through (see block arrow Ft1) a body 113*a* of a single Tesla valve 113. For example, an inlet 113*b* of the Tesla valve 113 receives the fluid sample. The inlet 113*b* of the Tesla valve 113 directs the fluid sample through a conduit 113*c* within the body 113*a* of the Tesla valve 113. The conduit 113*c* includes flow-control segments (113*d*, 113*e*) to direct the fluid sample in the one direction (see block arrow Ft1). The flow-control segments (113*d*, 113*e*) may be formed by projections 113*d* extending radially from the conduit 113*c* and partitions 113*e* provided within the projections 113*d*.

Still referring to FIG. 3D, the Tesla valve 113 may be oriented in a reverse direction to create high resistance and turbulence in the fluid sample flowing through the first Tesla valve 113. For example, the fluid sample will flow into the projections 113*d*, ricochet off the partitions 113*e*, deflect increasingly sharply before being rerouted around the partitions 113*e*, and mix within the conduit 113*c* (i.e., central passageway). The fluid sample will repeat the described flow path as the fluid sample continues to flow through the Tesla valve 113. By having the Tesla valve 113 oriented for a reverse direction flow path, the fluid sample will be further mixed before exiting an outlet 113*f* of the Tesla valve 113. From the outlet 113*f* of the Tesla valve 113, the fluid sample will exit the Tesla valve 113 and flow into a sensing section 120 of the multiphase sampler 110. In the sensing section 120, the fluid sample flows through a pipe 121. For example, an end of the pipe 121 is fluidly coupled to the outlet 113*f* of the Tesla valve 113. From the Tesla valve 113, the pipe 121 may extend axially in a horizontal direction of the plane P and the in a vertical direction of the plane P to fluidly couple to the horizontal section 16*a* of the production flow line 16.

In sensing section 120, a salinity sensor 130 is fluidly attached to the pipe 121 to measure a salinity (i.e., a concentration of salt) of the fluid sample. Multiple water-cut measurement techniques are sensitive to the water salinity. An inline salinity sensor based on microwaves or other principles may be used to measure the salinity changes in real-time so as to provide self-calibration of the water-cut measurement sensor. For example, the salinity sensor 130 may pass an electric current through the fluid sample. As the electric current is influenced by the salinity, the salinity sensor 130 will then measure a change in the electric current after passing through the fluid sample to determine the salinity (i.e., a concentration of salt) of the fluid sample. Additionally, the salinity sensor 130 may be wired to or wirelessly communicate with the control system 115. For example, the salinity sensor 130 may send data to the control system 115 (FIG. 1) and receive commands from the control system 115. From the sensing section 120, the fluid sample will flow back into the production flow line 16 via an outlet 218 of the multiphase sampler 110. For example, the outlet 218 of the multiphase sampler 110 is fluidly coupled to the horizontal section 16*a* of the production flow line 16 to receive the fluid sample.

Figure 4:
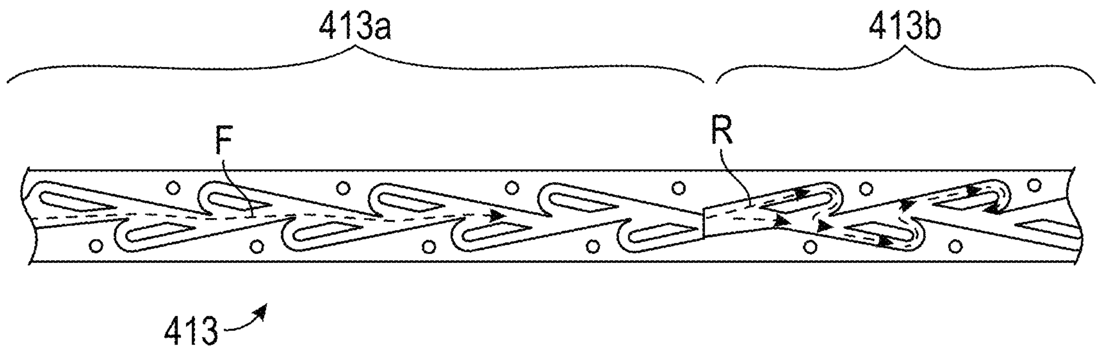
FIG. 4 illustrates a schematic diagram of a Tesla valve according to one or more embodiments of the present disclosure.

Now referring to FIG. 4, in one or more embodiments, a schematic diagram of a Tesla valve 413 that may be used in the multiphase sampler (110) is illustrated. The Tesla valve 413 may include a first Tesla valve 413*a* and a second Tesla valve 413*b* arranged back-to-back. The first Tesla valve 413*a* may be oriented to have a forward direction (indicated by dotted line F). In the first Tesla valve 413*a*, a fluid sample flows (see dotted line F) in a central passageway between the flow-control segments with only small lateral deflections. The second Tesla valve 413*b* may be oriented to have a reverse direction (indicated by dotted line R). In the second Tesla valve 413*b*, the fluid sample ricochets off (see dotted line R) the flow-control segments and deflecting increasingly sharply before being rerouted around the flow-control segments and mixing within the central passageway between the flow-control segments. In this way, the Tesla valve, e.g., the number of projections (in either direction), at the inlet and/or the outlet, may be selected or determined based on the expected flow-rate range of the target application (and the desired flow split between first vertical section 16*b* and the sample stream), such that accurate WLR measurements may be obtained. For example, the Tesla valve design may take into consideration the number of projections to ensure the flow through the sampling section is well-mixed and at a speed that allows for accurate WLR measurements.

Figure 5:
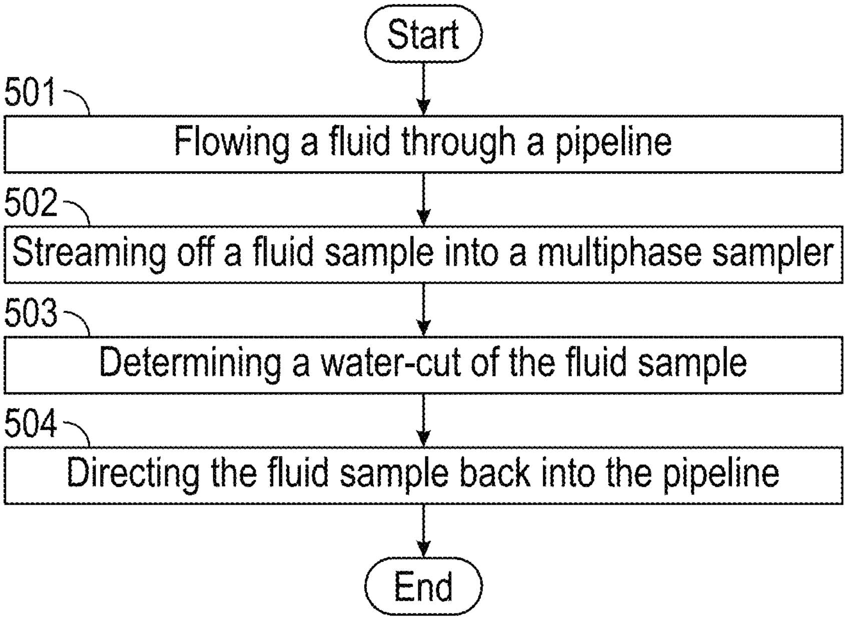
FIG. 5 illustrates a flowchart in accordance with one or more embodiments of the present disclosure.

Turning to FIG. 5, FIG. 5 shows a flowchart in accordance with one or more embodiments. Specifically, FIG. 5 describes a method for measuring a water-cut of fluids in accordance with embodiments disclosed herein. One or more blocks in FIG. 5 may be performed by one or more components (e.g., the water-cut measuring system 100, the multiphase sampler 110) as described in FIGS. 1-4. While the various blocks in FIG. 5 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 501, a fluid is flowed through a pipeline. For example, the fluid may be produced from a reservoir in a formation by drilling a wellbore into the formation, establishing a flow path between the reservoir and the wellbore, and conveying the fluids from the reservoir to a surface through the wellbore. At the surface, the fluid will flow through the pipeline fluidly connected to the wellbore. The pipeline conveys the fluid away from the wellbore. For example, the fluid may be transported, via the pipeline, to a separator for processing.

In Block 502, a fluid sample is streamed off the pipeline into a multiphase sampler. As the fluid flows through the pipeline, a volume of the fluid will be streamed into the multiphase sampler. This volume of the fluid represents a fluid sample of the fluid. The multiphase sampler may be installed and fluidly coupled to the pipeline during well operations. For example, an inlet of the multiphase sampler is fluidly coupled to the pipeline and an outlet of the multiphase sampler is fluidly coupled to the pipeline a distance away from the inlet. The inlet of the multiphase sampler includes a sharp bend from the pipeline which passively allows a well-mixed, representative (full-bore), liquid-dominant fluid sample to flow into the multiphase sampler. Additionally, the sharp bend ensures that the fluid sample is liquid-dominant by having gas in the fluid stay in the pipeline. For example, gas in the fluid will take a path of least resistance while liquids in the fluid (forming the fluid sample) will enter the inlet of the multiphase sampler due to the liquids having a higher inertia than gas. In some embodiments, the inlet of the multiphase sampler may be shaped in a conical funnel to capture and direct an entire bore/cross-section of the fluid sample into the multiphase sampler.

In the multiphase sampler, the fluid sample will flow through a first Tesla valve. The first Tesla valve may be oriented to have a reverse direction flow path to further mix the fluid sample. For example, in the first Tesla valve, the fluid sample flows into projections of the first Tesla valve. In the projections, the fluid sample ricochets off partitions of the first Tesla valve. After ricocheting off the partitions, the fluid sample deflects increasingly sharply and reroutes around the partitions to mix within a central passageway of the first Tesla valve. The fluid sample repeats this reverse direction flow path through an entire length of the first Tesla valve. The fluid sample will then exit out of the first Tesla valve and enter a sensing section of the multiphase sampler.

In Block 503, a water-cut of the fluid sample is determined in the sensing section of the multiphase sampler. For example, a water-cut sensor, fluidly attached to the sensing section, measures the water-cut of the fluid sample. To measure the water-cut, the water-cut sensor may pass radiation through the fluid sample and measure an optical transmission of the radiation at specific near-infrared wavelengths which correlates to the water-cut of the fluid sample. Additionally, the measured water-cut may be weighted against a flowrate of the fluid sample to determine an average water-cut, as described in Equation 1.

In some embodiments, instead of a water-cut sensor, a vertical column in the sensing section may measure the water-cut of the fluid sample. For example, the fluid sample fills up the vertical column over a period of time. Over this period of time, the fluid sample will separate in the vertical column. A liquid volume of the fluid sample will settle towards a bottom of the vertical column while a gas volume of the fluid sample will settle on top of the liquid volume of the fluid sample. To measure the water-cut of the fluid sample, a liquid-level of the liquid volume in the vertical column is measured. For example, a differential-pressure sensor may measure a differential pressure in the vertical column to determine a height (i.e., liquid-level) of the liquid volume. In some embodiments, a gas-liquid level gauge may send sonic pulse or electromagnetic/radar ping down the vertical column. The sonic pulse or electromagnetic/radar ping travels through the gas volume, reflects off a top level or interface of the liquid volume, and travels back to the gas-liquid level gauge. Based on the travel time of the sonic pulse or electromagnetic/radar ping, the gas-liquid level gauge determines a height (i.e., liquid-level) of the liquid volume. Based on the height (i.e., liquid-level) of the liquid volume, a liquid-faction ($\alpha_{liq}$) of the fluid sample in the vertical column is calculated. With the calculated liquid-faction ($\alpha_{liq}$), the water-cut of the fluid sample is calculated, as described in Equation 2.

In some embodiments, once the water-cut is determined, the fluid sample may flow through a second Tesla valve. The second Tesla valve may be oriented to have a forward direction flow path. For example, in the second Tesla valve, the fluid sample flows in a central corridor of the second Tesla valve. In the central corridor, the fluid sample will travel between projections and partitions of the second Tesla valve with only small lateral deflections. The second Tesla valve prevents the fluid from back flowing into the sensing section.

In Block 504, the fluid sample is directed back into the pipeline from the multiphase sampler. For example, the outlet of the multiphase sampler provides a pathway to direct the fluid sample back into the pipeline. In some embodiments, a pump may pump the fluid sample back into the pipeline.

Figure 6:
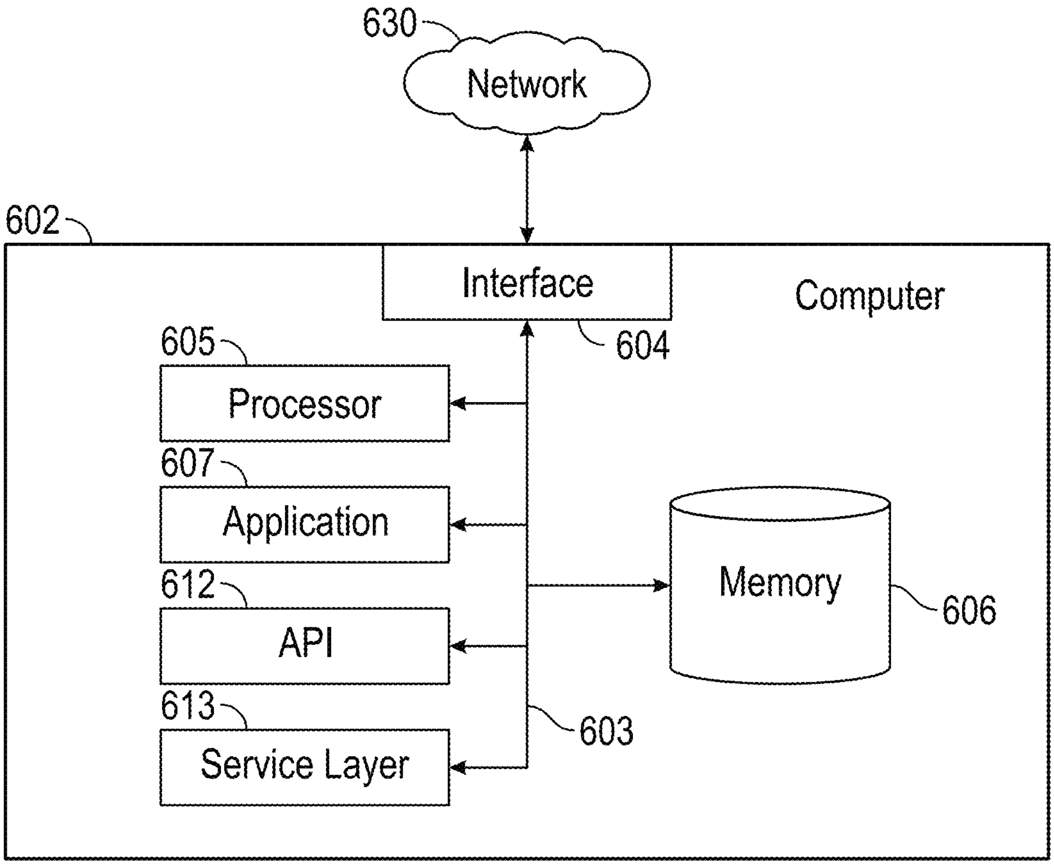
FIG. 6 illustrates a computer system in accordance with one or more embodiments.

Embodiments may be implemented on a computer system. FIG. 6 is a block diagram of a computer system 602 used to provide computational functionalities associated with described algorithms, methods, functions, processes, flows, and procedures as described in the instant disclosure, according to an implementation. The illustrated computer 602 is intended to encompass any computing device such as a high-performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer 602 may include a computer that includes an input device, such as a keypad, keyboard, touch screen, or other device that can accept user information, and an output device that conveys information associated with the operation of the computer 602, including digital data, visual, or audio information (or a combination of information), or a GUI.

The computer 602 can serve in a role as a client, network component, a server, a database or other persistency, or any other component (or a combination of roles) of a computer system for performing the subject matter described in the instant disclosure. The illustrated computer 602 is communicably coupled with a network 630. In some implementations, one or more components of the computer 602 may be configured to operate within environments, including cloud-computing-based, local, global, or other environment (or a combination of environments).

At a high level, the computer 602 is an electronic computing device operable to receive, transmit, process, store, or manage data and information associated with the described subject matter. According to some implementations, the computer 602 may also include or be communicably coupled with an application server, e-mail server, web server, caching server, streaming data server, business intelligence (BI) server, or other server (or a combination of servers).

The computer 602 can receive requests over network 630 from a client application (for example, executing on another computer 602) and responding to the received requests by processing the said requests in an appropriate software application. In addition, requests may also be sent to the computer 602 from internal users (for example, from a command console or by other appropriate access method), external or third-parties, other automated applications, as well as any other appropriate entities, individuals, systems, or computers.

Each of the components of the computer 602 can communicate using a system bus 603. In some implementations, any or all of the components of the computer 602, both hardware or software (or a combination of hardware and software), may interface with each other or the interface 604 (or a combination of both) over the system bus 603 using an application programming interface (API) 612 or a service layer 613 (or a combination of the API 612 and service layer 613. The API 612 may include specifications for routines, data structures, and object classes. The API 612 may be either computer-language independent or dependent and refer to a complete interface, a single function, or even a set of APIs. The service layer 613 provides software services to the computer 602 or other components (whether or not illustrated) that are communicably coupled to the computer 602. The functionality of the computer 602 may be accessible for all service consumers using this service layer. Software services, such as those provided by the service layer 613, provide reusable, defined business functionalities through a defined interface. For example, the interface may be software written in JAVA, C++, or other suitable language providing data in extensible markup language (XML) format or other suitable format. While illustrated as an integrated component of the computer 602, alternative implementations may illustrate the API 612 or the service layer 613 as stand-alone components in relation to other components of the computer 602 or other components (whether or not illustrated) that are communicably coupled to the computer 602. Moreover, any or all parts of the API 612 or the service layer 613 may be implemented as child or sub-modules of another software module, enterprise application, or hardware module without departing from the scope of this disclosure.

The computer 602 includes an interface 604. Although illustrated as a single interface 604 in FIG. 6, two or more interfaces 604 may be used according to particular needs, desires, or particular implementations of the computer 602. The interface 604 is used by the computer 602 for communicating with other systems in a distributed environment that are connected to the network 630. Generally, the interface 604 includes logic encoded in software or hardware (or a combination of software and hardware) and operable to communicate with the network 630. More specifically, the interface 604 may include software supporting one or more communication protocols associated with communications such that the network 630 or interface's hardware is operable to communicate physical signals within and outside of the illustrated computer 602.

The computer 602 includes at least one computer processor 605. Although illustrated as a single computer processor 605 in FIG. 6, two or more processors may be used according to particular needs, desires, or particular implementations of the computer 602. Generally, the computer processor 605 executes instructions and manipulates data to perform the operations of the computer 602 and any algorithms, methods, functions, processes, flows, and procedures as described in the instant disclosure.

The computer 602 also includes a memory 606 that holds data for the computer 602 or other components (or a combination of both) that can be connected to the network 630. For example, memory 606 can be a database storing data (e.g., pressure, temperature, density, fluid heigh, etc.) consistent with this disclosure. Although illustrated as a single memory 606 in FIG. 6, two or more memories may be used according to particular needs, desires, or particular implementations of the computer 602 and the described functionality. While memory 606 is illustrated as an integral component of the computer 602, in alternative implementations, memory 606 can be external to the computer 602.

The application 607 is an algorithmic software engine providing functionality according to particular needs, desires, or particular implementations of the computer 602, particularly with respect to functionality described in this disclosure. For example, application 607 can serve as one or more components, modules, applications, etc. Further, although illustrated as a single application 607, the application 607 may be implemented as multiple applications 607 on the computer 602. In addition, although illustrated as integral to the computer 602, in alternative implementations, the application 607 can be external to the computer 602.

There may be any number of computers 602 associated with, or external to, a computer system containing computer 602, each computer 602 communicating over network 630. Further, the term "client," "user," and other appropriate terminology may be used interchangeably as appropriate without departing from the scope of this disclosure. Moreover, this disclosure contemplates that many users may use one computer 602, or that one user may use multiple computers 602.

In some embodiments, the computer 602 is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

In addition to the benefits described above, the water-cut measuring system may improve an overall efficiency and performance at a well site while reducing cost and risk of non-productive time (NPT), and many other advantages. For example, the multiphase sampler presents no major interruptions to the main flow line (i.e., pipeline) as most of the flow continues down the main flow line. Additionally, the multiphase sampler may have no moving parts to make field implementation easier and decrease maintenance needs. In some embodiments, the multiphase sampler may reduce human intervention as the water-cut measurements may be continuously taken as long as the main flow line (i.e., pipeline) is being operated. Further, the water-cut measuring system may provide further advantages such as being able to decrease maintenance and operating cost, reduce human errors, and is not limited to any type of fluid (e.g., hydrocarbon, water, gas, CO2, and other fluids in either vapor or liquid phase).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed:

1. A system, comprising:

a pipeline for flowing a fluid therein; and a multiphase sampler fluidly coupled to the pipeline, wherein the multiphase sampler comprises:
an inlet to receive a fluid sample of the fluid from the pipeline;
at least one Tesla valve coupled between the pipeline and the inlet of the multiphase sampler to direct a flow of the fluid sample into a sensing section,
the sensing section having at least one sensor to determine a water-cut of the fluid sample; and
an outlet to return the fluid sample back into the pipeline.

2. The system of claim 1, wherein the inlet is fluidly coupled to a bend in the pipeline to provide an inertia on the fluid sample to form a liquid-dominant fluid sample.

3. The system of claim 2, wherein the inlet comprises a conical shape to capture and direct the liquid-dominant fluid sample into the at least one Tesla valve.

4. The system of claim 1, wherein the multiphase sampler comprises at least two Tesla valves, wherein a first Tesla valve is proximate the inlet and upstream of the sensing section and a second Tesla valve is downstream of the sensing section and proximate the outlet.

5. The system of claim 1, wherein the sensing section includes a column extending vertically upward to separate a liquid volume of the fluid sample from a gas volume of the fluid sample in the column, and wherein the at least one sensor is a differential pressure sensor to measure a differential pressure in the column.

6. The system of claim 1, wherein the at least one sensor is a near-infrared sensor, a microwave sensor, a differential pressure sensor, or a gas-liquid level gauge.

7. The system of claim 6, wherein the sensing section comprises a second sensor that is a pressure or temperature sensor.

8. The system of claim 1, further comprising a first pressure and temperature sensor fluidly coupled to the pipeline upstream of the inlet of the multiphase sampler and a second pressure and temperature sensor fluidly coupled to the pipeline downstream of the outlet of the multiphase sampler.

9. The system of claim 1, wherein the outlet comprises a reverse conical shape to prevent a backflow into the multiphase sampler.

10. A multiphase sampler, comprising:
an inlet to receive a fluid;
at least one Tesla valve coupled to the inlet to direct a flow of the fluid into a sensing section coupled to the at least one Tesla valve;
at least one sensor coupled to the sensing section to determine a water-cut of the fluid; and
an outlet coupled to the sensing section to allow the fluid to exit the multiphase sampler.

11. The multiphase sampler of claim 10, further comprising at least two Tesla valves, wherein a first Tesla valve is proximate the inlet and upstream of the sensing section and a second Tesla valve is downstream of the sensing section and proximate the outlet.

12. The multiphase sampler of claim 11, wherein the first Tesla valve is oriented in a reverse direction to have the fluid ricochet off flow-control segments of the first Tesla valve flow around the flow-control segments of the first Tesla valve, and wherein the second Tesla valve is oriented in a forward direction to have the fluid flow through a central passageway of the second Tesla valve between flow-control segments of the second Tesla valve.

13. The multiphase sampler of claim 11, wherein the first Tesla valve is oriented in a forward direction to have the fluid flow through a central passageway of the first Tesla valve between flow-control segments of the first Tesla valve, and wherein the second Tesla valve is oriented in a forward direction to have the fluid flow through a central passageway of the second Tesla valve between flow-control segments of the second Tesla valve.

14. The multiphase sampler of claim 10, further comprising a column vertically extending from the sensing section.

15. The multiphase sampler of claim 14, wherein the at least one sensor is a differential pressure sensor, and a gas-liquid level gauge is coupled near a top of the column.

16. The multiphase sampler of claim 10, wherein the at least one sensor is a near-infrared or microwave sensor.

17. The multiphase sampler of claim 10, further comprising a flushing port in the sensing section.

18. A method, comprising:
flowing a fluid through a pipeline;
streaming off a fluid sample from the fluid into an inlet of a multiphase sampler;
flowing the fluid sample through at least one Tesla valve of the multiphase sampler;
determining a water-cut of the fluid sample in a sensing section of the multiphase sampler; and
directing the fluid sample back into the pipeline.

19. The method of claim 18, wherein streaming off the fluid sample comprises:
flowing the fluid sample through a bend of the pipeline and into the inlet.

20. The method of claim 18, wherein determining the water-cut of the fluid sample comprises:
passing radiation from a sensor of the sensing section through the fluid sample and measuring an optical transmission of the radiation at specific near-infrared wavelengths which correlates to the water-cut of the fluid sample; or
filling a column vertically extending from the sensing section with the fluid sample, separating a liquid volume of the fluid sample in the column from a gas volume of the fluid sample in the column, measuring a height of the liquid volume in the column, and calculating a liquid-fraction of the fluid sample.

* * * * *